(12) United States Patent
Krämer (10) Patent No.: US 8,252,248 B2
(45) Date of Patent: Aug. 28, 2012

(54) ANALYTICAL TEST ELEMENT

(75) Inventor: Peter Krämer, Deidesheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1183 days.

(21) Appl. No.: 11/632,083

(22) PCT Filed: Jul. 5, 2005

(86) PCT No.: PCT/EP2005/007251
§ 371 (c)(1), (2), (4) Date: Jan. 8, 2007

(87) PCT Pub. No.: WO2006/005483
PCT Pub. Date: Jan. 19, 2006

(65) Prior Publication Data
US 2008/0031778 A1 Feb. 7, 2008

(30) Foreign Application Priority Data
Jul. 9, 2004 (DE) .......................... 10 2004 033 317

(51) Int. Cl.
*G01N 21/75* (2006.01)
*G01N 31/22* (2006.01)
*G01N 33/52* (2006.01)

(52) U.S. Cl. ........ 422/417; 422/400; 422/401; 422/408; 422/412; 422/420; 422/421; 422/422; 422/423; 422/424; 422/425; 422/426; 422/427; 422/428; 422/429; 422/68.1; 422/82.05; 422/82.06; 422/946; 422/947; 436/164; 436/169; 436/170; 435/13; 435/283.1; 435/287.1; 435/287.8; 435/287.9; 435/288.7

(58) Field of Classification Search .................... 422/57, 422/58, 56, 60, 946, 947, 400, 401, 408, 422/412, 417, 420, 421, 422, 423, 424, 425, 422/426, 427, 428, 429, 68.1, 82.05, 82.06; 436/169, 164, 170; 435/13, 283.1, 287.1, 435/287.7, 287.8, 287.9, 288.7
See application file for complete search history.

(56) References Cited

U.S. PATENT DOCUMENTS
4,473,457 A 9/1984 Columbus
(Continued)

FOREIGN PATENT DOCUMENTS
DE 102 0 296 A1 12/1957
(Continued)

*Primary Examiner* — Lyle Alexander
*Assistant Examiner* — Dennis M White
(74) *Attorney, Agent, or Firm* — Faegre Baker Daniels LLP (57) ABSTRACT

The invention relates to an analytical test element for analysis of a liquid sample. The analytical test element may contain a channel which is suitable for capillary transport of the liquid sample and which is provided with an inlet opening for the liquid sample and with an air outlet opening. At least one test field may be arranged in the channel, spaced apart from the inlet opening. The test element comprises a sample application site which is closed with a seal and which is designed in such a way that, when the seal is opened, the sample application site and the inlet opening of the channel are simultaneously open to the outside environment of the test element. The test element can then receive the liquid sample inside the channel via the sample application site and inlet opening, for analysis in the test field. The invention also relates to a test element magazine and to a system for analysis of liquid samples with at least one test element.

37 Claims, 3 Drawing Sheets

U.S. PATENT DOCUMENTS

| | | | |
|---|---|---|---|
| 4,549,952 A | 10/1985 | Columbus | |
| 4,654,127 A | 3/1987 | Baker et al. | |
| 4,957,582 A | 9/1990 | Columbus | |
| 5,035,704 A | 7/1991 | Lambert et al. | |
| 5,080,865 A * | 1/1992 | Leiner et al. | 422/68.1 |
| 5,165,292 A | 11/1992 | Prohaska | |
| 5,208,163 A * | 5/1993 | Charlton et al. | 436/63 |
| 5,354,692 A * | 10/1994 | Yang et al. | 436/514 |
| 5,489,414 A | 2/1996 | Schreiber et al. | |
| 5,505,308 A | 4/1996 | Eikmeier et al. | |
| 5,508,308 A | 4/1996 | Miller et al. | |
| 5,589,136 A | 12/1996 | Northrup et al. | |
| 5,636,640 A | 6/1997 | Staehlin | |
| 5,645,798 A | 7/1997 | Schreiber et al. | |
| 5,744,366 A | 4/1998 | Kricka et al. | |
| 5,863,502 A | 1/1999 | Southgate et al. | |
| 6,071,294 A | 6/2000 | Simons et al. | |
| 6,125,292 A * | 9/2000 | Uenoyama et al. | 435/14 |
| 6,451,264 B1 * | 9/2002 | Bhullar et al. | 422/100 |
| 6,475,436 B1 | 11/2002 | Schabbach et al. | |
| 6,497,845 B1 | 12/2002 | Sacherer | |
| 6,589,260 B1 | 7/2003 | Schmelzeisen-Redeker et al. | |
| 7,008,799 B1 | 3/2006 | Zimmer et al. | |
| 2002/0048819 A1 | 4/2002 | Alley | |
| 2002/0175075 A1 | 11/2002 | Deng et al. | |
| 2002/0187074 A1 * | 12/2002 | O'Connor et al. | 422/82.05 |
| 2003/0028125 A1 * | 2/2003 | Yuzhakov et al. | 600/583 |
| 2004/0039303 A1 | 2/2004 | Wurster et al. | |
| 2004/0067166 A1 * | 4/2004 | Karinka et al. | 422/82.03 |
| 2004/0116829 A1 * | 6/2004 | Raney et al. | 600/573 |
| 2005/0038357 A1 * | 2/2005 | Hartstein et al. | 600/583 |
| 2005/0136501 A1 * | 6/2005 | Kuriger | 435/14 |
| 2005/0214171 A1 | 9/2005 | Gestle et al. | |

FOREIGN PATENT DOCUMENTS

| | | |
|---|---|---|
| DE | 43 41 862 A1 | 6/1994 |
| DE | 198 54 316 A1 | 10/1999 |
| DE | 198 19 407 A1 | 11/1999 |
| DE | 100 01 116 A1 | 7/2001 |
| DE | 100 57 832 C1 | 2/2002 |
| EP | 0 503 379 A2 | 9/1992 |
| EP | 0 622 119 A1 | 11/1994 |
| EP | 0 622 626 B1 | 11/1994 |
| EP | 0 640 393 B1 | 3/1995 |
| EP | 0 732 590 A2 | 9/1996 |
| EP | 0 738 666 B1 | 10/1996 |
| EP | 0 924 520 A2 | 6/1999 |
| EP | 1 201 304 A2 | 5/2002 |
| EP | 1 486 766 A1 | 12/2004 |
| WO | WO 86/06488 | 11/1986 |
| WO | WO 99/29429 A1 | 6/1999 |
| WO | WO 01/68238 A2 | 9/2001 |
| WO | WO 01/89383 A2 | 11/2001 |
| WO | WO 01/89691 A2 | 11/2001 |
| WO | WO 02/08753 A2 | 1/2002 |
| WO | WO 03/020134 A2 | 3/2003 |
| WO | WO 2004/010760 A2 | 2/2004 |
| WO | WO 2004/091403 A1 | 10/2004 |

* cited by examiner

ANALYTICAL TEST ELEMENT

CROSS-REFERENCE TO RELATED APPLICATIONS

This application is a nationalization of PCT Patent Application Serial No. PCT/EP2005/007251, filed Jul. 5, 2005, which claims priority to German Patent Application Serial No. 10 2004 033 317.3, filed Jul. 9, 2004, the disclosures of which are expressly incorporated herein by reference.

FIELD OF THE INVENTION

The present invention relates to an analytical test element, to a test element magazine with a multiplicity of analytical test elements, and to a system for analysis of liquid samples with at least one analytical test element.

BACKGROUND OF THE INVENTION

For analysis of samples, for example body fluids such as blood or urine, test element analysis systems are often used in which the samples to be analyzed are applied to a test element and, if appropriate, react with one or more reagents in a test field on the test element before they are analyzed. Optical, in particular photometric, evaluation of test elements is one of the most common methods used for rapid determination of the concentration of analytes in samples. Photometric evaluations are generally used in the fields of analysis, environmental analysis and, above all, in medical diagnostics. Test elements that are evaluated photometrically have an important place, particularly in the field of blood glucose diagnosis from capillary blood.

Portable measurement appliances for blood sugar determination have become increasingly popular in recent years. They allow blood sugar measurement values to be determined at any desired time by means of an easy-to-use measurement appliance, a puncture aid, optimized in terms of the pain caused by the puncture, and a disposable test element, and in this way they permit more precise insulin doses for stabilizing the patient's blood sugar value. Most of the presently available blood sugar measurement appliances involve separate individual test elements, measurement appliances and puncture aids. The individual test elements are removed from a moisture-proof individual package by the patient. Blood is obtained by puncturing the skin with a puncture aid. A required minimum amount of blood is then applied to the test element, and a measurement is carried out using the measurement appliance.

There are different kinds of test elements. For example, substantially square slides are known in the middle of which a multilayer test field is located. Diagnostic test elements of strip shape are referred to as test strips. The prior art discloses capillary test elements for spatial separation of the detection zone and the sample application site of a test element.

WO 99/29429 relates to an analytical test element for determination of an analyte in a liquid, with an inert carrier, a detection element and a channel that permits capillary transport of liquid, and with a sample application opening at one end and an air outlet opening at the other end of the channel for the capillary transport of liquid. The channel permitting capillary transport of liquid is at least partially formed by the carrier and the detection element and extends, in the direction of capillary transport, from the sample application opening as far as the edge of the detection element lying closest to the air outlet opening.

The package holding the respective test element is designed to satisfy the main conditions for maintaining the function of the chemical and biochemical components on the test element during a long storage period. These conditions are, in particular, protection against the effects of light, protection against entry of moisture, dirt, microbes and dust, and protection against mechanical deterioration of the test elements.

As an alternative to individual packages, storage containers are known which contain a multiplicity of individually removable test elements and provide a sufficiently large amount of desiccant for absorbing the moisture introduced by opening and removal of a test element, thereby ensuring a sufficient storage period for all the test elements contained in the container. A storage container of this kind is known from EP 0 640 393 B1. In the storage container, the test elements are held as in a quiver, from which they can be removed when the storage system is opened.

Another suitable form of a storage container for test elements are aluminum or plastic tubes that are closed by a press-on or screw-on stopper. These storage containers have the disadvantage that the individual test elements have to be manually removed in an awkward way. A patient, for example one who wishes to perform a blood sugar test, has to carry around not just the measurement appliance, but also a puncture aid and a separate test element storage container. Besides this inconvenience, a particular disadvantage is that, when a test element is removed, this test element and/or another one is contaminated, and the contamination can lead to incorrect measurement results. There is a danger of test strips becoming contaminated by dirt adhering to the patient's hands or by the test element falling out.

Another known alternative is for a certain number of test elements to be stored in the measurement appliance itself.

DE 198 19 407 discloses a container for blood sugar measurement appliances or other measurement appliances operating with disposable test strips that can be fed to a sensor for measurement purposes, said container comprising two parts, in the first of which the test strips are stored, and in the second of which the used test strips are collected. The test elements can be arranged alongside one another so that they form a band, which can be wound rather like the tape in an audio cassette. Instead of this, they can also be arranged so as to form a round plate, on which they are placed at a defined distance from one another in the area of the plate circumference, so that, when the plate is rotated, a new test field comes into the corresponding measurement position. Another possibility is for the test strips to form a stack from which they are individually removed by a mechanism, and the test strips are brought one after another into the corresponding measurement position and, after the measurement, are brought into a collecting chamber.

EP 0 622 119 A1 discloses substantially rectangular magazines with mutually parallel chambers lying alongside one another in a line.

When the test elements are stored in the measurement appliance itself, the storage container, or the chamber in which a test element is located, is opened by an opening mechanism, and the test element is brought by a movement mechanism into a sample application position.

DE 198 54 316 A1 describes a storage container with separate moisture-proof chambers for test elements. Each of the chambers has at least two openings lying opposite one another and each closed by a sealing film. To remove the test elements, a test element is pushed out of its chamber with the aid of a ram. The ram cuts through the sealing film on one side of the chamber and then presses on the test element which, because of this pressure from the ram, cuts through the sealing film on the opposite side, so that the test element can be pushed out of the chamber. Other mechanisms for automatic removal of test elements from a storage container are disclosed in EP 0 738 666 B1 for a storage container in the form of a drum, in EP 0 662 626 B1 and EP 0 732 590 A2 for a storage container in the form of a disk, and in WO 02/08753 A2 for stacked storage of the test elements.

After a sample (for example blood) has been applied to the removed test element, detection and measurement data evaluation take place in the measurement appliance. After removal of the test element by the patient, or by another mechanism integrated in the appliance, the storage container is automatically positioned such that a further measurement can take place.

In the prior art, the test elements are normally protected, in particular against entry of moisture, by sealing the storage container or by sealing individual chambers of the storage container for the test elements. The sealing is provided, for example, in the form of a suitable film material with low water-vapor permeability (for example aluminum film coated with adhesive plastic). Moreover, the test elements are often protected against moisture by a desiccant being introduced into the storage container or into the chambers.

The devices known in the prior art, which integrate the provision of test elements, the sample application function and the measurement function within the measurement appliance, have the disadvantage that their construction is very complex. This complexity arises in particular from the fact that each test element has to be transported to different positions within the device (from the storage container to the sample application site, to the measurement position and then to the disposal site). Moreover, the test elements in the prior art have to be protected in an elaborate manner against moisture in particular. The filling and sealing of the storage container, integrated in the device and serving for storage of the test elements, is a cost-intensive and time-consuming procedure.

DE 100 57 832 C1 describes a blood analysis appliance with a simplified construction, which forms a complete system consisting of a puncture element, a blood collection device, test elements comprising a test field, and an evaluation means. The test elements are inserted into a magazine and, in order to carry out a number of measurements, can be brought one after another into a working position. When a respective test element is positioned in the working position, a puncture element can be pushed through the test element and inserted into the surface of a user's skin. The blood emerging from the surface of the skin impacts directly on the test element. This blood analysis appliance has the disadvantage that the test field itself is pierced, with the result that toxic components of the test field may remain adhering to the puncture aid and may be carried into the puncture wound in the user's skin.

SUMMARY OF THE INVENTION

An object of the present invention is therefore to make available an analytical test element, a test element magazine, and a system for analysis of liquid samples with at least one analytical test element, all of these avoiding the abovementioned disadvantages of the prior art. Entry of moisture into the test elements is to be avoided in particular. The production of the test elements, of the test element magazine and of the analysis system is also to be simplified, and their complexity reduced.

According to an exemplary embodiment of the invention, this object is achieved by an analytical test element for analysis of a liquid sample, containing a channel which is suitable for capillary transport of the liquid sample and which is provided with an inlet opening for the liquid sample and with an air outlet opening, at least one test field being arranged inside the channel at a distance from the inlet opening, the test element comprising a sample application site which is closed with a seal and which is designed in such a way that, when the seal is opened, the sample application site and the inlet opening of the channel are simultaneously open toward the outside environment of the test element, and the test element can receive the liquid sample inside the channel via the sample application site and inlet opening, for analysis in the test field.

The test element according to an exemplary embodiment of the invention has the advantage that the test element itself is closed off by the seal in a manner substantially impermeable to water vapor and preventing entry of dirt and, therefore, for the period of use in the appliance, no separate storage means is needed for protection against entry of moisture or contaminants. The step of unpacking a test element prior to a measurement being carried out can thus be dispensed with, thereby resulting in simplified handling for the user and in a simpler construction of a measurement appliance in which the test elements are already integrated. When the seal is opened at the sample application site, the inlet opening of the channel is also opened, so that the test element can be made ready for use in just a single opening procedure. The channel suitable for capillary transport of the liquid sample, and with integrated test field, has the advantage that the liquid sample is transported automatically by the capillary forces to the test element that represents the detection area. The sample to be analyzed can be placed directly on the sample application site.

The air outlet opening ensures release of air from the channel during the capillary transport of the liquid sample to the test field via the inlet opening in the channel. In the test element according to the exemplary embodiment of the invention, it may already be open to the outside environment of the test element before the seal is opened. A contamination of the test field via the air outlet opening can in this case be avoided by suitable routing of the channel. In another embodiment of the present invention, the air outlet opening leads into a sufficiently large hollow space which is closed off from the outside environment of the test element and which allows air to be released from the channel via the air outlet opening, without having to open the hollow space to the outside environment. It is also possible for the air outlet opening to be separately sealed, and to be opened to the outside environment of the test element by opening of this separate seal. In a preferred embodiment of the present invention, the sample application site, the inlet opening of the channel and the air outlet opening of the channel are all simultaneously opened to the outside environment of the test element by opening of just one seal.

The test field is arranged in the channel preferably between the inlet opening and the air outlet opening. In a preferred embodiment of the present invention, the inlet opening is arranged at one end of the channel, and the air outlet opening is arranged at the other end of the channel. The liquid sample passes through the inlet opening and into the channel and fills the latter at least until the test field is wetted, whereupon one or more components of the liquid sample are preferably analyzed photometrically or electrochemically. A homogeneous wetting of the test field with a sample quantity defined by the channel diameter is also guaranteed, thereby increasing the precision and reproducibility of the measurement. A further advantage of the test element according to an exemplary embodiment of the invention is that the test field is not damaged during opening (by piercing, cutting or tearing) and is not contaminated by detached remnants of the seal.

In the test element according to an exemplary embodiment of the invention, the seal is to be made from a material that is substantially impermeable to water vapor, for example an aluminum film coated with a polymer.

In a preferred embodiment of the present invention, the inlet opening and, if appropriate, the air outlet opening of the channel lead into a free space in the test element, said free space being arranged such that, when the seal is opened, it is open to the outside environment of the test element. In the unused state of the test element, the free space is preferably at least partially delimited on one side by the seal closing the sample application site and, on a second side remote from the first side, is at least partially delimited by a second seal. This arrangement has the advantage that a piercing device (for example a lancet, needle, knife, cannula, spike) can first open the second seal on the side remote from the sample application site and then, by way of the free space, can also open the seal of the sample application site. This permits a simplified construction of an integrated measurement system, since the application site for the liquid sample and the piercing device can be arranged on opposite sides of the test element, and the piercing device is therefore not in the way of the sample being applied. Moreover, the piercing device can also serve as a perforating device which, in addition to opening the two seals, also perforates the patient's skin for collecting a sample, so that body fluid emerging from the perforation in the skin can then pass as liquid sample directly into the test element. To do this, the patient does not have to perform any other maneuvers or movements, and he or she does not require any additional equipment.

In a preferred embodiment of the present invention, the channel in the test element has a U-shaped or V-shaped course. This course has the advantage of space-saving accommodation of the channel in the test element. The channel ends can in this case be arranged one above the other or alongside one another in a free space contained in the test element.

Since, in a preferred case where the channel has a substantially rectangular cross section, one dimension of the channel, for example its height, is fixed by the physical limits of the capillary action, the volume of the capillary channel can be adapted by suitable choice of the two other dimensions, for example length and width. The height, in the case of aqueous liquid samples, is preferably less than 1 mm, particularly preferably less than 0.5 mm. The width of the channel can preferably be less than 5 mm, particularly preferably less than 2 mm, and the total length of the channel can preferably be less than 5 cm, particularly preferably less than 2 cm.

In a preferred embodiment of the present invention, the distance from the sample application site to the inlet opening of the channel is less than the distance from the sample application site to the air outlet opening of the channel. This has the advantage that the liquid sample entering the test element at the sample application site passes into the inlet opening and not into the air outlet opening of the channel, since the air outlet opening is intended to remain free of sample liquid, so as to permit escape of air as the channel is being filled.

The channel, in the area of the inlet opening, preferably has a better wettability by the liquid sample than it does in the area of the air outlet opening. This measure is likewise intended to promote entry of the liquid sample into the inlet opening of the channel and to prevent its entry into the air outlet opening. Moreover, in its interior, the channel between the inlet opening and the at least one test field preferably has a better wettability by the liquid sample than it does between the at least one test field and the air outlet opening. This can be achieved by hydrophobic treatment of the air outlet opening and/or of the adjoining areas of the channel that are not to be wetted.

In a preferred embodiment of the present invention, the seal closing the sample application site has, on the side directed toward the interior of the test element, a better wettability by the liquid sample than it does on the side directed away from the interior of the test element. This has the advantage that, upon direct placement of the liquid sample to the pierced seal at the sample application site, the outside of the seal is poorly wetted by the sample. This therefore promotes transport of the sample to the better wetted inner side of the seal, and, consequently, its desired transport into the test element.

In a preferred embodiment of the present invention, a desiccant is contained in the test element. This desiccant can further enhance the protection of the test element against moisture, as it absorbs moisture. The desiccant can, for example, be contained in the channel, in proximity to the air outlet opening. Solid desiccants can be used, for example, as said desiccant. The desiccant, in one embodiment, preferably contains zeolite or silica gel. Zeolite or silica gel can be used in the form of beads or tablets, but also in the form of hot-melt adhesives containing silica gel or zeolite fillers and applied as films, as employed in the packaging industry.

In a preferred embodiment of the present invention, the test element contains a waste area for receiving an excess of liquid sample in the test element. The waste area serves to avoid undesired filling of certain areas of the test element, in particular of the channel in the area of the air outlet opening, with liquid sample.

The seal closing the sample application site, in one embodiment, preferably has a pre-structuring which is configured such that, when the seal is opened, a defined ridge is obtained. The defined ridge or protrusion should have clear edges that facilitate transport of the liquid sample into the test element. The defined geometry and dimension of the ridge or protrusion ensures that there is a greater probability of the liquid sample coming into contact with the capillary channel and being sucked into the interior of the channel. A possible pre-structuring is cross-shaped or star-shaped, with a surrounding rectangle or a surrounding circle being added to define the length of the protrusion.

In a preferred embodiment of the present invention, the test element contains a detection window which is directed toward the test field and which serves for photometric analysis of the liquid sample on the test field. Light emitted from a light source, and light reflected from the test field, can pass through the detection window, the latter being transparent in the relevant wavelength range. A detector can detect the reflected light, and the detected signals can be processed by electronics and the result shown to the user on a display device.

In a preferred embodiment of the present invention, conductor tracks for electrochemical analysis of the liquid sample on the test field are formed in at least one wall delimiting the channel. These conductor tracks are required for electrochemical analysis of the liquid sample in the test field of the test element. A simultaneous photometric and electrochemical analysis is also conceivable.

In a preferred embodiment of the present invention, the test element is built up from a multiplicity of layers. This has the advantage of simplified production. The different properties, for example wettability, optical transparency, stability and shape, of different areas of the test element can be achieved by corresponding configuration of the individual layers that are connected to one another.

In the test element constructed in a layered formation, the channel can extend through one or more layers. The whole channel or partial areas of the channel can be produced by cutting out or punching out part of one or more layers. A U-shaped or V-shaped channel is accordingly produced by punching out or cutting out a U-shaped or V-shaped area from a single intermediate layer, or correspondingly shaped areas from several layers subsequently stacked on one another (for example two rectangular areas in two intermediate layers, between which a carrier layer is arranged that connects the two rectangular channel sections via an opening). The channel height is in this case fixed by the thickness of the intermediate layer. A free space in the test element can likewise be produced by cutting out or punching out areas of corresponding shape in one or more layers.

The analytical test element according to an exemplary embodiment of the invention, built up in a layered formation, comprises at least one sealing layer. A first sealing layer is used as a seal for the sample application site (with the properties described above) and, to permit use of the test element, is opened by piercing, cutting, tearing off, etc. (preferably by piercing). Other sealing layers, for example on that side of the test element remote from the first sealing layer, or on its end faces arranged at 90° relative thereto, can serve to protect the test element against moisture and contaminants and, if appropriate, can also be partially opened, in addition to the first sealing layer, upon use of the test element.

In a preferred embodiment of the present invention, the sealing layer has a hydrophobic coating. The first sealing layer preferably has a hydrophobic coating on its outside, in order to achieve the abovementioned better wettability by the aqueous liquid sample on its inside compared to its outside.

The test element according to an exemplary embodiment of the invention, built up in a layered formation, preferably comprises at least one carrier layer and at least one intermediate layer at least partially containing the channel. The carrier layers give stability to the test element. They can, for example, delimit the channel as bottom and top layers and can include the test field. These bottom and top layers can contain hydrophilic materials and/or have surfaces with a hydrophilic finish in selected areas (preferably between inlet opening and test field). In this context, hydrophilic surfaces are surfaces that attract water. Aqueous samples, including blood, spread well on such surfaces. The latter are easily wetted by these samples. Such surfaces are characterized, inter alia, by the fact that a water droplet forms an acute wetting angle or contact angle on them at the interface. By contrast, on hydrophobic surfaces, i.e. surfaces that repel water, an obtuse wetting angle is formed at the interface between water droplet and surface.

The wetting angle resulting from the surface tensions of the sample liquid and of the surface being tested is a measure of the hydrophilicity of a surface. Water, for example, has a surface tension of 72 mN/m. If the surface tension of the surface in question is far below this value, i.e. more than 20 mN/m below this value, the wetting is poor, and the resulting wetting angle is obtuse. Such a surface is designated as hydrophobic. As the surface tension approaches the value found for water, the wetting is good, and the wetting angle is acute. By contrast, if the surface tension is equal to or greater than the value found for water, the droplet runs, and there is total spreading of the liquid. A wetting angle can then no longer be measured. Surfaces that form an acute wetting angle with droplets of water, or in which total spreading of a droplet of water is observed, are designated as hydrophilic.

The capacity of a capillary to take up liquid is associated with the wettability of the channel surface with the liquid. For aqueous samples, this means that a capillary should be made from a material whose surface tension comes close to 72 mN/m or exceeds this value.

Examples of sufficiently hydrophilic materials, for the construction of a capillary that rapidly takes up aqueous samples, are glass, metal or ceramic. For use in test elements, however, these materials are not quite so suitable, because they have certain disadvantages, for example the risk of breaking of glass or ceramic, or a change in the surface properties of many metals over time. Therefore, plastic films or molded parts are normally used for production of test elements. Generally, the plastics used scarcely ever exceed a surface tension of 45 mN/m. Even with what are relatively speaking the most hydrophilic plastics, for example polymethylmethacrylate (PMMA) or polyamide (PA), it is only possible to construct capillaries with very slow suctioning power (if any). Capillaries made from untreated hydrophobic plastics, for example polystyrene (PS), polypropylene (PP) or polyethylene (PE), basically do not take up any aqueous samples. Hence the requirement that the plastics used as construction material for test elements with capillary channels have to be rendered hydrophilic.

In a preferred embodiment of the analytical test element according to an exemplary embodiment of the invention, at least one surface, but preferably two surfaces, particularly preferably two opposite surfaces, of the surfaces forming the inner face of the channel for capillary liquid transport is/are made hydrophilic. If more than one surface is made hydrophilic, said surfaces can be made hydrophilic by identical or different methods. Hydrophilic treatment is especially required if the materials forming the capillary channel, in particular the carrier layers, are themselves hydrophobic or only slightly hydrophilic, for example because they are made from nonpolar plastics.

The hydrophilic treatment of the surface of the capillary channel is ideally undertaken by using for its production, in particular for the production of the carrier layers, a hydrophilic material which does not itself take up the sample liquid, or does so only to an inappreciable extent. Where this is not possible, the hydrophilic treatment of a hydrophobic or only very slightly hydrophilic surface can be achieved by suitable coating with a stable hydrophilic layer inert to the sample material, for example by covalent bonding of photoreactive, hydrophilic polymers to a plastic surface, by application of layers containing wetting agent, or by coating of surfaces with nanocomposites by sol-gel technology. It is also possible to obtain an increased hydrophilicity by thermal, physical or chemical treatment of the surface.

The hydrophilic treatment is very particularly preferably achieved, in one embodiment, by using thin layers of oxidized aluminum. These layers are either applied directly to the desired parts of the test element, for example by vacuum vapor deposition of the workpieces with metallic aluminum and subsequent oxidation of the metal, or in the form of metal films or metal-coated plastic films for the test element construction, which also have to be oxidized to achieve the desired hydrophilicity. Metal layer thicknesses of 1 to 500 nm are sufficient in this respect. The metal layer is then oxidized to produce the oxidized form, particularly suitable methods, besides electrochemical anodic oxidation, having proven to be oxidation in the presence of water vapor or boiling in water. Depending on the method used, the oxide layers thereby obtained are between 0.1 and 500 nm thick, preferably between 10 and 100 nm thick. Greater layer thicknesses, both of the metal layer and of the oxide layer, can also be attained in practice.

The carrier layers serving as the top and bottom layers of the channel can also have hydrophobic materials, or comprise a hydrophobic surface coating, in selected areas (preferably between air outlet opening and test field). This is intended to ensure poor wettability of the carrier layer surface by the aqueous liquid samples, for example in order to avoid the samples entering the area of the channel at the air outlet opening and thus blocking this area.

In the context of an exemplary embodiment of this invention, an intermediate layer is understood as a layer which is arranged between two carrier layers and which at least partially contains the channel, and whose thickness defines the capillary height of at least parts of the channel. Intermediate layers can be two-sided adhesive tapes or can be connected directly, or by means of adhesion promoters, to the carrier layers serving as the bottom and top layers. The intermediate layers can be provided with hydrophobic fillers that reduce their permeability to water vapor, so that the channel is protected against moisture entering via the intermediate layers. As an alternative to this, the intermediate layers themselves can be made from hydrophobic materials.

In a particularly preferred embodiment of the present invention, the layers are arranged in the following sequence:
A) a first sealing layer comprising the sample application site,
B) a transparent first carrier layer,
C) a first intermediate layer containing a first part of the channel,
D) a second carrier layer containing an opening,
E) a second intermediate layer containing a second part of the channel,
F) a third carrier layer, and
G) a second sealing layer,
where the opening in the second carrier layer connects the first part of the channel to the second part of the channel, and a test field is arranged in the first part of the channel, and, when the test element is not in use, a free space extends through the layers B) to F), into which free space the first and second parts of the channel open. The outside face of the first sealing layer, and those sides of the second and third carrier layers directed toward the second part of the channel, can have a hydrophobic coating. A desiccant can be arranged in the second part of the channel. The first sealing layer can contain a detection window for photometric analysis of the liquid sample on the test field. The intermediate layers are preferably hydrophobic. Those sides of the first and second carrier layers directed toward the first part of the channel are preferably hydrophilic or have a hydrophilic coating.

In a preferred embodiment of the present invention, the seal or the sealing layer is a composite film that comprises an aluminum film, an outer layer of PE, PET or oriented PA, and an inner layer of PE, PP or lacquers, or comprises a high-barrier composite of PET/SiOx.

The invention, in an exemplary embodiment, further relates to a test element magazine designed as a band, drum, stack or disk. In the case of a band, a large number of test elements according to the invention are arranged contiguous with one another, so that they can be wound up on a reel, for example. By rotating the reel, a new test element can be brought into a working position (sample removal and/or measurement position). The reel can be driven manually or automatically.

A test element magazine designed as a drum preferably has the shape of a substantially cylindrical, elongate drum in which chambers for receiving the test elements are arranged in a star shape around the longitudinal axis of the drum. The length of the drum is in principle adapted to the length of the test elements that are to be accommodated therein. The bottom and top surfaces of the cylindrical drum contain the openings of the chambers which, because of the individual sealing of the test elements in accordance with an exemplary embodiment of the invention, do not have to be closed. However, suitable measures should be taken to ensure that the test element is held in the chamber in a manner secure against slipping, until its removal from the drum.

In the case of a stack, the individual test elements lie above one another in a storage container and can be brought individually to the corresponding measurement position. In an exemplary embodiment of the present invention, the storage container containing the stack requires no further measures to be taken for protecting the test elements, because they already each have a seal in accordance with an exemplary embodiment of the invention.

In the case of a disk, the individual test elements are arranged radially and at a defined distance from one another on a substantially round plate. A new test element can be brought into a working position by rotation of the disk, said rotation being able to be done manually or automatically.

The invention in an exemplary embodiment further relates to a system for analysis of liquid samples with at least one test element magazine according to the invention, with a piercing device for opening the seal of a test element at the sample application site shortly before application of a liquid sample, and with a detector for analysis of the liquid sample in the test field of a test element. The detector is, for example, a device for photometric or electrochemical evaluation of test elements. In this context, a piercing device is understood as a device that can open the seal of a respective test element according to the invention by pushing through it or cutting it. In an exemplary embodiment, it has pointed or sharp edges for this purpose. It can, for example, be in the form of a spike, a needle, a lancet, a knife or a cannula.

In one embodiment of the present invention, the system contains, in addition to the piercing device, also a perforating device in the form of a lancet, a cannula, a needle, a knife or a spike, for producing a perforation in the skin of a patient, so as to collect a body fluid as liquid sample. Alternatively, however, the piercing device itself can also serve as the perforating device. The perforating device is used to create an opening in the body through which a body fluid can emerge. In the case where the piercing device itself serves as the perforating device, it is advantageous if the test element comprises at least two seals which are arranged on opposite sides of the test element and which require a slight piercing force, and if a free space is present in the test element between these seals, so that the piercing device serving as perforating device can be pushed through the test element (and the free space) and can be inserted into the surface of a user's skin. The body fluid emerging from the surface of the skin can impact directly on the sample application site of the test element.

In the case of two separate piercing and perforating devices, the perforating device can be surrounded concentrically by the piercing device. This permits space-saving accommodation of both devices in the analysis system according to the invention. A further advantage of this arrangement is that the test element is located in the working position simultaneously for both devices.

In another embodiment of the present invention, the piercing device and the perforating device are arranged next to one another in a holder and, by rotation of the holder, can be brought in succession into a working position.

The test element magazine is preferably designed as a band of successive, individually sealed test elements, the system comprising a transport device which is configured in such a way that it can transport one test element at a time into a working position, in which the seal of the test element can be opened by the piercing device. In another preferred embodiment, the test element magazine is designed as a disk on which the test elements are arranged radially, one test element at a time being able to be rotated, by rotation of the disk, into a working position in which the seal of the test element can be opened by the piercing device.

The system according to an exemplary embodiment of the invention preferably comprises a compression unit for increasing the pressure on the perforated skin of the patient upon withdrawal of the body fluid. This compression unit serves to promote the flow of the body fluid out of the opening in the body. This can be a compression unit of the kind disclosed in WO 01/89383. The user presses the body part, from which the sample is to be collected, against the optionally deformable compression unit. The user keeps the body part in this compressed state during creation of an opening in the skin and/or during the withdrawal of the body fluid.

The invention further relates to the use of an analytical test element according to the invention for analyzing the glucose content in blood or in interstitial fluid.

BRIEF DESCRIPTION OF THE DRAWINGS

The invention is explained in more detail below with reference to the drawing, in which.

DETAILED DESCRIPTION OF THE DRAWINGS

Figure 1:
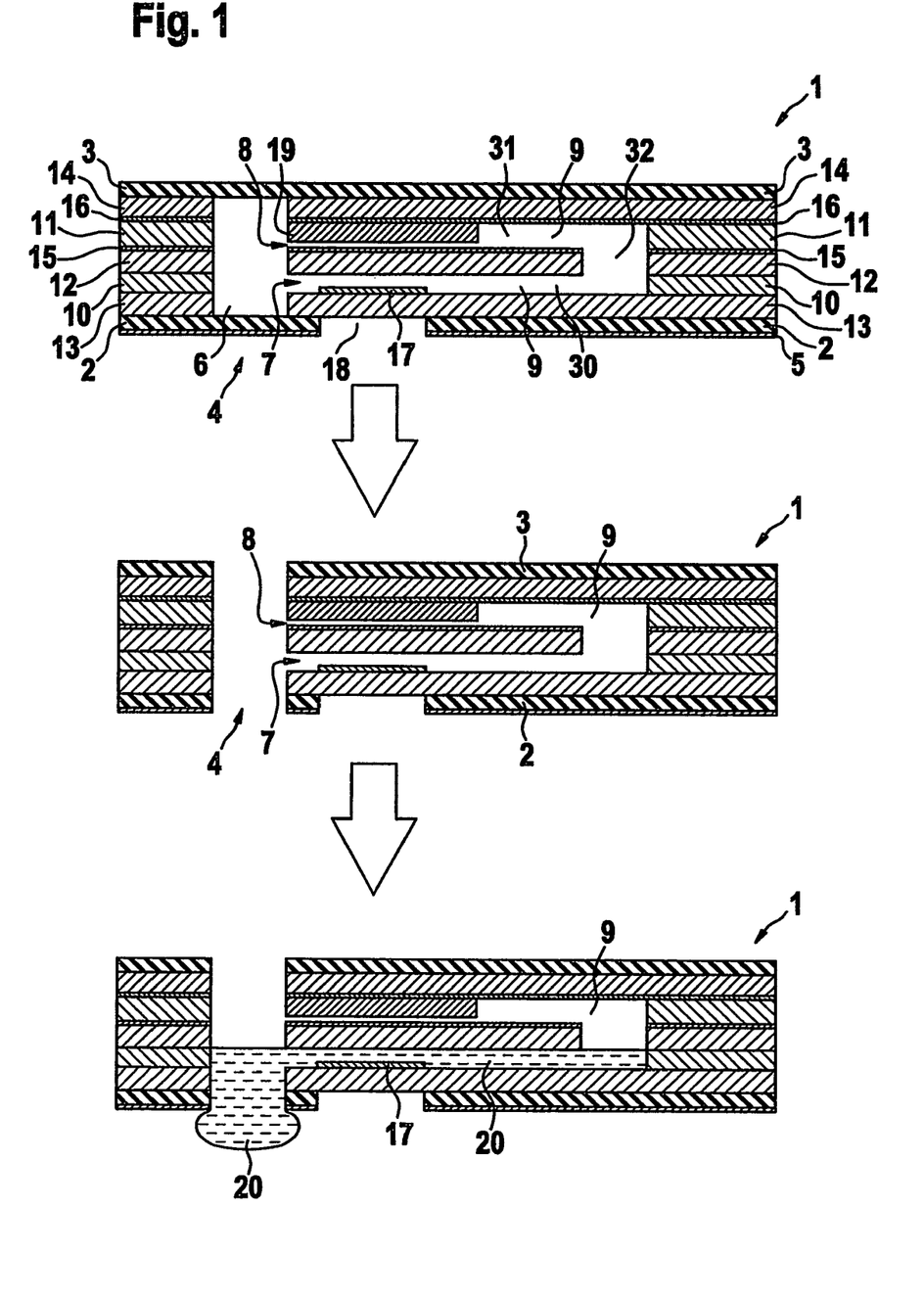
FIG. 1 shows the cross section of an illustrative embodiment of an analytical test element according to the invention, in the sealed state, in the opened state, and in the state with a liquid sample applied.

FIG. 1 shows an illustrative embodiment of an analytical test element according to the invention in the sealed state, in the opened state, and in the state with a liquid sample applied.

The top view in FIG. 1 shows the test element 1 in the sealed state. It is built up from a multiplicity of layers. On both outer faces, it is sealed by first and second sealing layers (2 and 3 respectively) which have low permeability to water vapor. The first sealing layer 2 closes the sample application site 4 and has a hydrophobic coating 5 on its outside, so that an aqueous liquid sample does not wet the outside but instead passes into the test element 1 when the seal is opened at the sample application site 4. In the test element 1 there is a free space 6 into which there lead an inlet opening 7 and an air outlet opening 8 of a channel 9 suitable for capillary transport of a liquid sample. The channel 9 is U-shaped and extends over several layers, namely two intermediate layers 10, 11 (first and second parts 30, 31 of the channel) and a carrier layer 12 (opening 32). In addition to this second carrier layer 12, the test element 1 also comprises a transparent first carrier layer 13 and, arranged adjacent to the second sealing layer 3, a third carrier layer 14. The carrier layers 12, 13, 14 form the top and bottom layers of the channel 9. The second and third carrier layers 12, 14 each have, on their side directed toward the channel 9, a hydrophobic coating 15, 16, respectively, which is intended to prevent the aqueous liquid sample from passing into that part of the channel 9 directed toward the air outlet opening 8. Arranged in the channel 9, on the side directed toward the transparent first carrier layer 13, there is a test field 17 on which the liquid sample can be analyzed. On that side of the transparent first carrier layer 13 directed away from the test field 17, there is a detection window 18 in the first sealing layer 2 for photometric analysis of the liquid sample on the test field 17. In the channel 9, near the air outlet opening 8, a desiccant is provided which is intended to absorb possible residual moisture in the sealed test element 1.

The middle view in FIG. 1 shows an opened test element 1 in which both sealing layers 2, 3 have been pierced or cut open in the area of the free space 6. The sample application site 4 is now open and is ready to receive a liquid sample. With the first sealing layer 2 opened at the sample application site 4, the inlet opening 7 of the channel 9 and the air outlet opening 8 of the channel 9 are also simultaneously open to the outside environment of the test element 1.

The bottom view in FIG. 1 shows how the liquid sample 20 reaches the test field 17. A sufficiently large droplet of the liquid sample 20 is applied to the test element 1 at the sample application site 4, from where the liquid sample 20 passes through the free space 6 to the inlet opening 7 of the channel 9 and is sucked into the latter by capillary forces. In the channel 9, the sample 20 flows across the test field 17, where it is analyzed.

Figure 2:
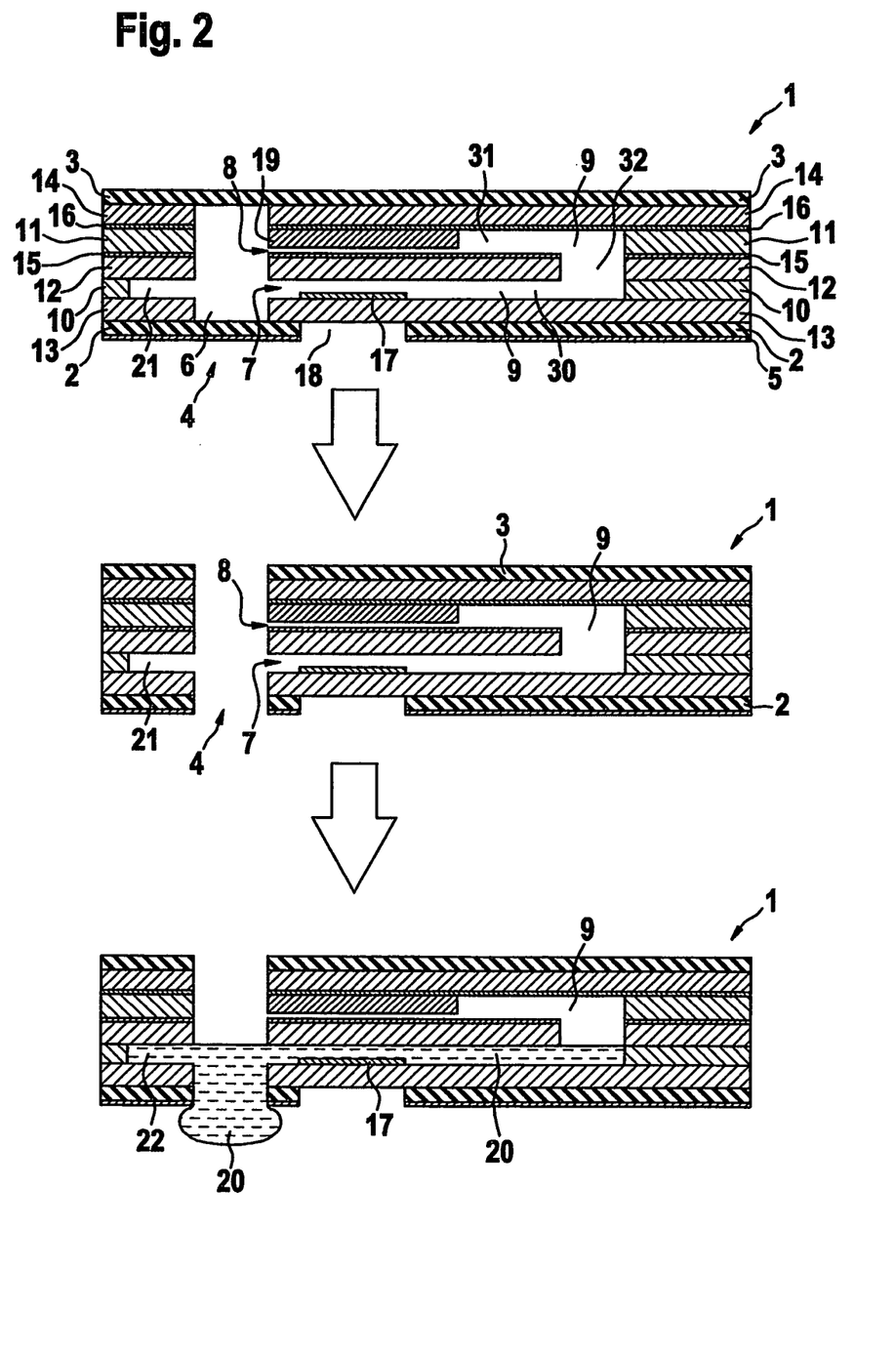
FIG. 2 shows the cross section of an illustrative embodiment of an analytical test element according to the invention, with a waste area, FIGS. 3.1-3.3 show an illustrative embodiment of a system according to the invention for analysis of liquid samples with a test element magazine according to the invention in the form of a band, with a piercing device and with a detector.

FIG. 2 shows an illustrative embodiment of another analytical test element according to the invention whose structure corresponds to the test element shown in FIG. 1 and which additionally has a waste area 21 that can receive an excess 22 of liquid sample 20. As regards the rest of the structure, the description of FIG. 1 also applies to the test element 1 according to FIG. 2, and the reference numbers have the same meaning as in FIG. 1.

Figure 31:
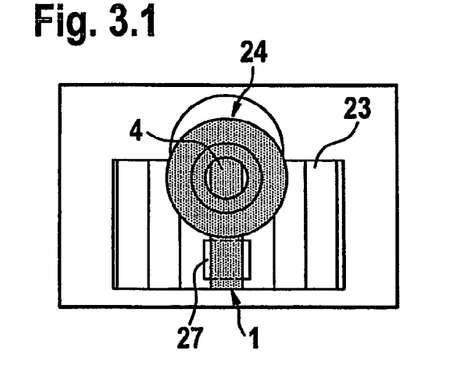
Figure 32:
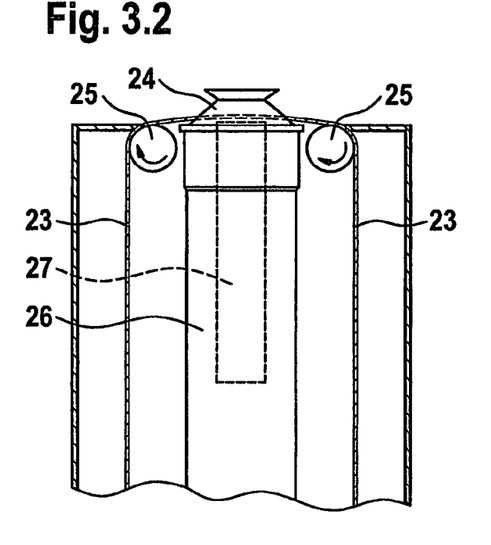
Figure 33:
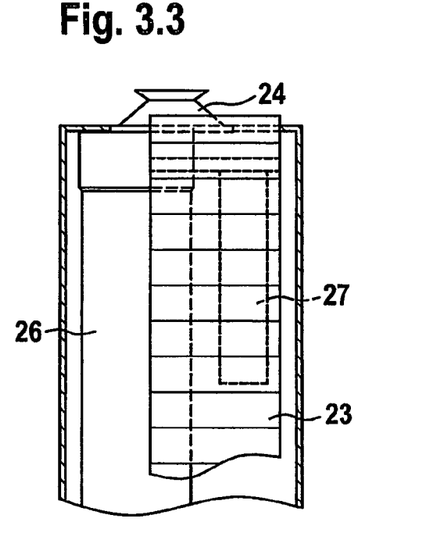

FIGS. 3.1-3.3 are a schematic representation of an illustrative embodiment of a system according to the invention for analysis of liquid samples.

The top left view in FIG. 3.1 shows a schematic plan view of the system. The test elements 1 according to the invention are present as a magazine in the form of a band 23. An expression cone serves as compression unit 24 for increasing the pressure on the area of the patient's skin surrounding the opening made in the body, so as to convey a body fluid, such as blood or interstitial fluid, from the opening in the body. The compression unit 24 is in this case arranged over the sample application site 4 of a test element 1 situated in the working position.

The bottom left view in FIG. 3.2 is a schematic representation of a first side view of the same system according to the invention. The magazine in the form of a band 23 runs across two transport rollers 25, in order to bring one test element 1 at a time to the working position, in which the compression unit 24 is located directly above the sample application site. Located in the cylindrical arrangement 26 represented in FIG. 3, there are (not shown) a piercing device and, if appropriate, a perforating device which, for example by rotation of a holder that holds them, can be brought in succession into the working position, that is to say into a position in which the piercing device can pierce the seal on both sides of the test element 1 (in particular at the sample application site), and the perforating device can produce an opening in a part of the body placed on the compression unit 24. In front of the cylindrical arrangement there is a detector 27, for example for photometric analysis of a sample, which detector 27 is directed at a detection window (not shown) in the test element 1 in the working position.

The bottom view on the right in FIG. 3.3 is a schematic representation of a second side view of the same system according to the invention. The cylindrical arrangement 26, the detector 27, the band-shaped magazine 23 and the compression unit 24 can again be clearly seen.

Figure 4:
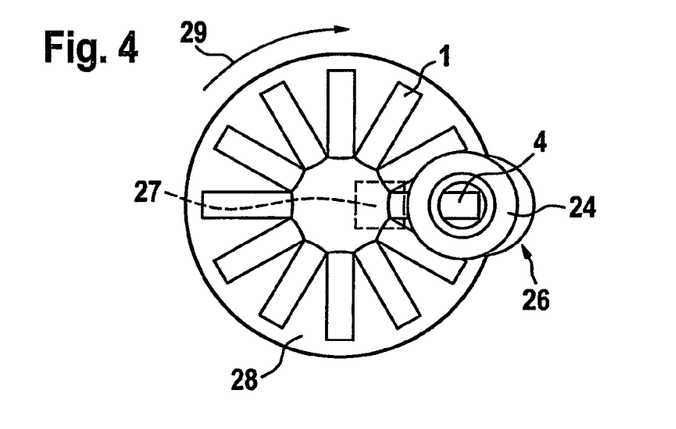
FIG. 4 shows an illustrative embodiment of a system according to the invention for analysis of liquid samples with a test element magazine according to the invention in the form of a disk.

FIG. 4 is a schematic plan view of an illustrative embodiment of another system according to the invention for analysis of liquid samples.

The system contains a magazine in the form of a disk 28 on which the test elements 1 according to the invention are arranged radially on a substantially round plate. By rotating the magazine 28 in the direction of rotation 29, one test element 1 at a time can be brought into the working position (sample application site 4 under the compression unit 24). The system further contains a piercing device (not shown), which is accommodated in a cylindrical arrangement 26, and also a detector 27.

LIST OF REFERENCE NUMBERS 1 test element
2 first sealing layer
3 second sealing layer
4 sample application site
5 hydrophobic coating
6 free space
7 inlet opening
8 air outlet opening
9 channel
10 first intermediate layer
11 second intermediate layer
12 second carrier layer
13 first carrier layer
14 third carrier layer
15 hydrophobic coating
16 hydrophobic coating
17 test field
18 detection window
19 desiccant
20 liquid sample
21 waste area
22 excess of liquid sample
23 magazine in form of a band
24 compression unit
25 transport rollers
26 cylindrical arrangement
27 detector
28 magazine in form of a disk
29 rotation direction
30 first part of the channel
31 second part of the channel
32 opening

The invention claimed is:

1. A test element for analysis of a liquid sample, the test element comprising:
a channel which is suitable for capillary transport of the liquid sample and which is provided with an inlet opening for the liquid sample and with an air outlet opening,
a free space inside the test element, the inlet opening and the air outlet opening each being contiguous with the free space,
at least one test field being arranged inside the channel at a distance from the inlet opening,
the test element comprises a sample application site which is closed with a seal, and which is configured such that, when the seal is opened, the sample application site, the inlet opening of the channel, the air outlet opening of the channel, and the free space are simultaneously opened toward an outside environment of the test element, the sample application site being accessible for direct application of the liquid sample from outside the test element to be received inside the channel via flow of the liquid sample through the sample application site, the free space, and then through the inlet opening, for analysis in the at least one test field, wherein the seal is opened by one of being pierced and being cut.

2. The test element as claimed in claim 1, wherein the inlet opening is arranged at one end of the channel, and the air outlet opening is arranged at the other end of the channel.

3. The test element as claimed in claim 1, wherein in an unused state of the test element, the free space is at least partially delimited on a first side by the seal closing the sample application site and, on a second side remote from the first side, is at least partially delimited by a second seal.

4. The test element as claimed in claim 1, wherein the channel in the test element has one of a U-shaped course and a V-shaped course.

5. The test element as claimed in claim 1, wherein the channel has a substantially rectangular cross section and has a width of less than 5 mm and a height of less than 1 mm.

6. The test element as claimed in claim 1, wherein the channel has a total length of less than 5 cm.

7. The test element as claimed in claim 1, wherein the distance from the sample application site to the inlet opening of the channel is less than the distance from the sample application site to the air outlet opening of the channel.

8. The test element as claimed in claim 1, wherein the channel, in an area of the inlet opening, has an increased wettability by the liquid sample than in the area of the air outlet opening.

9. The test element as claimed in claim 1, wherein in an interior of the channel, a first area of the channel between the inlet opening and the at least one test field has an increased wettability by the liquid sample than a second area of the channel between the at least one test field and the air outlet opening.

10. The test element as claimed in claim 1, wherein the seal closing the sample application site has, on the side directed toward an interior of the test element, an increased wettability by the liquid sample than it does on the side directed away from the interior of the test element.

11. The test element as claimed in claim 1, wherein a desiccant is contained in the test element.

12. The test element as claimed in claim 11, wherein the desiccant contains one of a zeolite gel and a silica gel.

13. The test element as claimed in claim 1, further comprising a waste area for receiving an excess of liquid sample in the test element.

14. The test element as claimed in claim 1, wherein the test element contains a detection window which is directed toward the test field and which serves for photometric analysis of the liquid sample on the test field.

15. The test element as claimed in claim 1, wherein in at least one wall delimiting the channel, conductor tracks are provided for electrochemical analysis of the liquid sample on the test field.

16. The test element as claimed in claim 1, wherein the test element is built up from a multiplicity of layers.

17. The test element as claimed in claim 16, wherein the channel extends through at least one layer of the multiplicity of layers.

18. The test element as claimed in claim 16, wherein the test element comprises at least one sealing layer.

19. The test element as claimed in claim 18, wherein the at least one sealing layer has a hydrophobic coating.

20. The test element as claimed in claim 16, wherein the test element comprises at least one carrier layer and at least one intermediate layer at least partially containing the channel.

21. The test element as claimed in claim 16, wherein the multiplicity of layers are arranged in the following sequence:
   A) a first sealing layer comprising the sample application site,
   B) a transparent first carrier layer,
   C) a first intermediate layer containing a first part of the channel,
   D) a second carrier layer containing an opening,
   E) a second intermediate layer containing a second part of the channel,
   F) a third carrier layer, and
   G) a second sealing layer,
   wherein the opening in the second carrier layer connects the first part of the channel to the second part of the channel, and the at least one test field is arranged in the first part of the channel, and, when the test element is in an unused state a free space extends through the layers B) to F), into which free space the first and second parts of the channel open.

22. The test element as claimed in claim 21, wherein an outside face of the first sealing layer, and those sides of the second and third carrier layers directed toward the second part of the channel, have a hydrophobic coating.

23. The test element as claimed in claim 21, wherein a desiccant is arranged in the second part of the channel.

24. The test element as claimed in claim 21, wherein the first sealing layer contains a detection window for photometric analysis of the liquid sample on the test field.

25. The test element as claimed in claim 21, wherein the first and the second intermediate layers are hydrophobic.

26. The test element as claimed in claim 21, wherein those sides of the first and second carrier layers directed toward the first part of the channel are one of hydrophilic and have a hydrophilic coating.

27. The test element as claimed in claim 1, wherein the seal is one of a composite film that comprises an aluminum film, an outer layer of one of a PE, a PET and an oriented PA, and an inner layer of one of a PE, a PP and lacquers; and a high-barrier composite of PET/SiOx.

28. A test element magazine comprising a multiplicity of test elements as claimed in claim 1, wherein the test element magazine is configured as one of a band, a drum, a stack, and a disk.

29. A system for analysis of liquid samples comprising at least one test element as claimed in claim 1, a piercing device for opening the seal of the at least one test element at the sample application site of the at least one test element shortly before application of a liquid sample, and a detector for analysis of the liquid sample in the test field of the at least one test element.

30. The system as claimed in claim 29 further comprising a compression unit for increasing the pressure on the perforated skin of the patient upon withdrawal of the body fluid.

31. The test element of claim 1, wherein the test element is configured for analyzing the glucose content in blood or in interstitial fluid.

32. The system as claimed in claim 29, wherein the piercing device also serves as a perforating device.

33. A test element for analysis of a liquid sample, the test element comprising:
   a channel which is suitable for capillary transport of the liquid sample and which is provided with an inlet opening for the liquid sample and with an air outlet opening,
   a free space inside the test element, the inlet opening and the air outlet opening each being interfaced with the free space,
   at least one test field being arranged inside the channel at a distance from the inlet opening, and
   a sample application site which is closed with a seal,
   the test element being configured such that, when the seal is opened by one of being pierced and being cut, the sample application site, the inlet opening of the channel, the air outlet opening of the channel, and the free space are simultaneously opened toward an outside environment of the test element, and the free space is in flow communication with the channel through the inlet opening, and the channel is in flow communication with the free space through the air outlet opening.

34. A test element for analysis of a liquid sample, the test element comprising:
   a channel which is suitable for capillary transport of the liquid sample and which is provided with an inlet opening for the liquid sample,
   a free space inside the test element,
   at least one test field being arranged inside the channel at a distance from the inlet opening, and
   a sample application site which is closed with a seal, the test element being configured such that, when the seal is opened by one of being pierced and being cut, the sample application site, the inlet opening of the channel, and the free space are simultaneously opened toward an outside environment of the test element,
   the channel further including an air outlet opening positioned such that during the capillary transport of the liquid sample inside the channel to the at least one test field, the air outlet opening ensures release of air from the channel to the free space, the inlet opening and the air outlet opening being contiguous with the free space.

35. A test element for analysis of a liquid sample, the test element comprising:
   a free space inside the test element;
   a channel which is suitable for capillary transport of the liquid sample and which is provided with an inlet opening for the liquid sample at an interface with the free space and with an air outlet opening at another interface with the free space,
   at least one test field being arranged inside the channel at a distance from the inlet opening, and
   a sample application site which is closed with a seal,
   the test element being configured such that, when the seal is opened, the channel is opened toward an outside environment of the test element, and the test element can receive the liquid sample inside the channel via the sample application site and then through the inlet opening, for analysis in the at least one test field,
   wherein the channel includes a first portion that extends from the inlet opening, away from the free space, toward the test field, and a second portion that extends away from the test field, toward the free space, to the air outlet opening.

36. A test element for analysis of a liquid sample, the test element comprising:

a channel which is suitable for capillary transport of the liquid sample and which is provided with an inlet opening for the liquid sample and with an air outlet opening, a free space separate from the channel, the inlet opening and the air outlet opening each being disposed between the channel and the free space, and each being contiguous with the free space, at least one test field being arranged inside the channel at a distance from the inlet opening, and a sample application site which is closed with a seal, the test element being configured such that, when the seal is opened by one of being pierced and being cut, the sample application site, the inlet opening of the channel, the air outlet opening of the channel, and the free space are simultaneously opened toward an outside environment of the test element, and the test element can receive the liquid sample inside the channel via the sample application site and then through the inlet opening, for analysis in the at least one test field.

37. A test element for analysis of a liquid sample, the test element comprising:

a channel which is suitable for capillary transport of the liquid sample and which is provided with an inlet opening for the liquid sample and with an air outlet opening, a free space inside the test element, the inlet opening and the air outlet opening being interfaced with the free space, at least one test field being arranged inside the channel at a distance from the inlet opening, and a sample application site which is closed with a seal, the test element being configured such that, when the seal is opened by one of being pierced and being cut, the sample application site, the inlet opening of the channel, the air outlet opening of the channel, and the free space are simultaneously opened toward an outside environment of the test element, and the liquid sample, once applied, passes through the sample application site, then through the free space, and is drawn by capillary force through the inlet opening, into the channel and onto the test field for analysis.

* * * * *